United States Patent
Kang et al.

(10) Patent No.: US 11,591,305 B2
(45) Date of Patent: Feb. 28, 2023

(54) METHOD FOR PRODUCING FISETIN OR FISETIN DERIVATIVES

(71) Applicant: DAEGU CATHOLIC UNIVERSITY INDUSTRY ACADEMIC COOPERATION FOUNDATION, Gyeongsan-si (KR)

(72) Inventors: Dong Wook Kang, Seoul (KR); Min Gi Chu, Daegu (KR); Seok Ju Lee, Gyeongsan-si (KR); Eun Jung Lee, Wonju-si (KR)

(73) Assignee: DAEGU CATHOLIC UNIVERSITY INDUSTRY ACADEMIC COOPERATION FOUNDATION, Gyeongsan-si (KR)

( * ) Notice: Subject to any disclaimer, the term of this patent is extended or adjusted under 35 U.S.C. 154(b) by 0 days.

(21) Appl. No.: 17/570,420

(22) Filed: Jan. 7, 2022

(65) Prior Publication Data

US 2022/0220088 A1    Jul. 14, 2022

(30) Foreign Application Priority Data

Jan. 11, 2021    (KR) .................. 10-2021-0003607

(51) Int. Cl.
*C07D 311/32*    (2006.01)

(52) U.S. Cl.
CPC .................. *C07D 311/32* (2013.01)

(58) Field of Classification Search
CPC ...................................... C07D 311/32
See application file for complete search history.

(56) References Cited

PUBLICATIONS

Borsari et al. J. Med. Chem. 2016, 59, 7598-7616 (Year: 2016).*
Venkateswarlu et al. Tetrahedron 2005, 61, 3013-3017 (Year: 2005).*
Vyas et al. Jour. Indian Chem. Soc. 1930, 27, 189-190 (Year: 1930).*
Cabrera et al. "Synthetic chaicones, flavanones, and flavones as antitumoral agents: Biological evaluation and structure-activity relationships" Bioorg. Med. Chem. 15:3356-3367 (2007).
Chahal et al. "Synthesis, Spectral Characterization and Antimicrobial Activity of Copper(II), Cobalt(II) and Zinc(II) Complexes of 6-Methoxy-3-Formylchromone" IJPSR 8(8):3471-3476 (2017).
Chiruta et al. "Chemical Modification of the Multitarget Neuroprotective Compound Fisetin" J. Med. Chem. 55:378-389 (2012).

* cited by examiner

*Primary Examiner* — Matthew P Coughlin
(74) *Attorney, Agent, or Firm* — Myers Bigel, P.A.

(57) ABSTRACT

The present invention provides a method for producing fisetin or fisetin derivatives, which is capable of mass production. The method for producing fisetin or fisetin derivatives according to the present invention is capable of mass-producing fisetin or fisetin derivatives without a purification process such as a column chromatography process.

9 Claims, No Drawings

METHOD FOR PRODUCING FISETIN OR FISETIN DERIVATIVES

BACKGROUND

1. Technical Field

This application claims the benefit of the filing date of Korean Patent Application No. 10-2021-0003607 filed with the Korean Intellectual Property Office on Jan. 11, 2021, the entire contents of which are incorporated herein by reference.

The present invention relates to a method for producing fisetin or fisetin derivatives. Specifically, the present invention relates to a method for producing fisetin or fisetin derivatives, which is capable of mass production.

2. Related Art

As a kind of flavonol, fisetin having a structure of the following Formula 1 is currently being studied as a therapeutic agent for various diseases, and has been found to exhibit various therapeutic activities such as anticancer, neuroprotective, and antioxidant activities. In particular, fisetin has been reported as a potential therapeutic agent that acts to inhibit β-amyloid aggregation in Alzheimer's disease. β-amyloid aggregation causes nerve damage, and fisetin has been found to improve memory by activating a signaling pathway in the hippocampus. It has also been reported that fisetin extends lifespan, reduces markers of tissue aging, and reduces age-related problems.

[Formula 1]

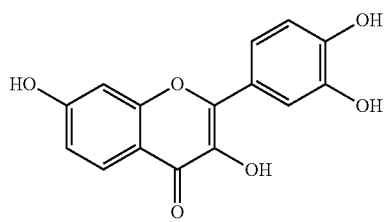

Although fisetin-related studies require a large amount of fisetin, the amount of fisetin that can be extracted from natural sources is limited. A conventional method for synthesizing fisetin is performed using paeonol or quercetin as a starting material.

However, this method requires an expensive starting material and compound separation by column chromatography in each step, and hence is not suitable for mass production of fisetin and necessarily has a reduced product yield. Accordingly, there is a need to develop an efficient method for synthesis of fisetin.

SUMMARY

An object of the present invention is to provide a production method capable of mass-producing fisetin or fisetin derivatives.

However, the object to be achieved by the present invention is not limited to the above-mentioned object, and other objects not mentioned herein will be clearly understood by those skilled in the art from the following description.

According to one aspect of the present invention, there is provided a method for producing fisetin or fisetin derivatives, the method including steps of: producing a first mixture containing 1-(2-hydroxy-4-methoxy-phenyl)-ethanone and 1-(2,4-dimethoxy-phenyl)-ethanone by methylating 1-(2,4-dihydroxy-phenyl)-ethanone; producing a second mixture containing a chalcone compound by adding the first mixture and a benzaldehyde compound represented by the following Formula 2 to a basic solution and allowing them to react; and producing fisetin derivatives represented by the following Formula 3 by adding hydrogen peroxide to the second mixture:

[Formula 2]

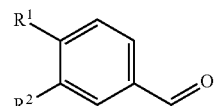

[Formula 3]

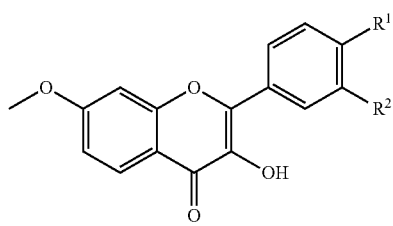

In Formula 2 and Formula 3, $R^1$ and $R^2$ are each independently an alkoxy group containing a linear or branched alkyl group having 1 to 4 carbon atoms or a cyclic alkyl group having 3 to 6 carbon atoms; or a hydrogen atom.

The method for producing fisetin or fisetin derivatives according to one embodiment of the present invention may provide fisetin or fisetin derivatives with high purity and high yield without separately performing an intermediate purification process.

The method for producing fisetin or fisetin derivatives according to one embodiment of the present invention may provide fisetin or fisetin derivatives with high purity and high yield by using a recrystallization process instead of column chromatography.

The method for producing fisetin or fisetin derivatives according to one embodiment of the present invention may provide fisetin or fisetin derivatives with high purity and high yield without separately purifying and separating the chalcone compound as an intermediate product.

Effects of the present invention are not limited to the above-described effects, and effects not mentioned herein will be clearly understood by those skilled in the art from the present specification and the accompanying drawings.

DETAILED DESCRIPTION

Throughout the present specification, it is to be understood that when any part is referred to as "including" any component, it does not exclude other components, but may further include other components, unless otherwise specified.

Throughout the present specification, the unit "parts by weight" may refer to the ratio of weight between components.

Throughout the present specification, "A and/or B" means "A and B, or A, or B".

Throughout the present specification, the expression "perform a reaction" may means stirring a reaction mixture for a specific time while maintaining the reaction mixture within a specific temperature range.

Hereinafter, the present invention will be described in more detail.

According to one embodiment of the present invention, there is provided a method for producing fisetin or fisetin derivatives, the method including steps of: producing a first mixture containing 1-(2-hydroxy-4-methoxy-phenyl)-ethanone and 1-(2,4-dimethoxy-phenyl)-ethanone by methylating 1-(2,4-dihydroxy-phenyl)-ethanone; producing a second mixture containing a chalcone compound by adding the first mixture and a benzaldehyde compound represented by the following Formula 2 to a basic solution and allowing them to react; and producing fisetin derivatives represented by the following Formula 3 by adding hydrogen peroxide to the second mixture:

[Formula 2]

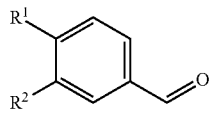

[Formula 3]

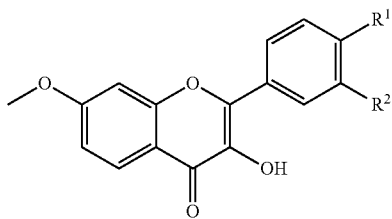

In Formula 2 and Formula 3, $R^1$ and $R^2$ are each independently an alkoxy group containing a linear or branched alkyl group having 1 to 4 carbon atoms or a cyclic alkyl group having 3 to 6 carbon atoms; or a hydrogen atom.

The method for producing fisetin or fisetin derivatives according to one embodiment of the present invention may provide fisetin or fisetin derivatives with high purity and high yield without separately performing an intermediate purification process. In addition, the method may provide fisetin or fisetin derivatives with high purity and high yield by using a recrystallization process instead of column chromatography. Furthermore, the method may provide fisetin or fisetin derivatives with high purity and high yield without separately purifying and separating the chalcone compound as an intermediate product.

Hereinafter, each step of the production method of the present invention will be described in more detail.

First, 1-(2,4-dihydroxy-phenyl)-ethanone is prepared. The 1-(2,4-dihydroxy-phenyl)-ethanone may be prepared by purchasing a commercially available one, or may be prepared by direct production. When 1-(2,4-dihydroxy-phenyl)-ethanone is produced, 1-(2,4-dihydroxy-phenyl)-ethanone may be produced by a method used in the art, and the production method is not particularly limited.

According to one embodiment of the present invention, the 1-(2,4-dihydroxy-phenyl)-ethanone may be produced by Friedel-Crafts acylation of resorcinol and recrystallization.

The Friedel-Crafts acylation is a reaction for acylating an aromatic ring, which may be an electrophilic aromatic substitution reaction. The resorcinol, 1,3-dihydroxybenzene, may be acylated by Friedel-Crafts acylation to produce 1-(2,4-dihydroxy-phenyl)-ethanone.

According to one embodiment of the present invention, 1-(2,4-dihydroxy-phenyl)-ethanone may be produced by subjecting the resorcinol to Friedel-Crafts acylation with acetic anhydride in the presence of boron trifluoride-diethyl ether. The boron trifluoride-diethyl ether may be added as a catalyst for Friedel-Crafts acylation.

Specifically, acylation of the resorcinol may be performed by adding a solution containing boron trifluoride-diethyl ether and an organic solvent dropwise to a solution containing the resorcinol, acetic anhydride and an organic solvent, followed by stirring at a temperature of 50° C. to 100° C. for 10 hours to 15 hours. As the organic solvent, one used in the art may be used. For example, ethyl acetate may be used, but the present invention is not limited thereto.

After completion of the acylation reaction, 1-(2,4-dihydroxy-phenyl)-ethanone may be obtained through steps of: diluting the resulting product with water, followed by extraction with an organic solvent; washing the organic layer; removing water from the organic layer; concentrating the filtrate under reduced pressure; and recrystallizing the concentrate.

By diluting the resulting product with water, it is possible to remove the catalyst and by-products having high solubility in water, and to separate the desired product 1-(2,4-dihydroxy-phenyl)-ethanone with an organic solvent. The extracting step may be performed once or twice or more, and when it is performed several times, 1-(2,4-dihydroxy-phenyl)-ethanone may be obtained in high yield.

According to one embodiment of the present invention, the step of washing the organic layer may include washing the organic layer with a weakly basic aqueous solution, and may be performed once or twice or more. The weakly basic aqueous solution may be a saturated aqueous solution of $NaHCO_3$, and the pH thereof may be about 8 to 10. When the organic layer is washed as described above, it is possible to remove acetic acid that may be produced as a by-product during the acylation reaction.

According to one embodiment of the present invention, the step of removing water from the organic layer may be performed using $MgSO_4$, but is not limited thereto, and may also be performed using other hygroscopic compounds or other drying methods.

According to one embodiment of the present invention, the step of concentrating the filtrate under reduced pressure may serve to remove the remaining organic solvent and water, and may be performed by a method used in the art.

According to one embodiment of the present invention, the concentrate may be recrystallized. In a conventional art, 1-(2,4-dihydroxy-phenyl)-ethanone as a product is obtained by column chromatography. However, the column chromatography process takes a very long time and requires a lot of cost, and the amount of compound obtained using the column chromatography process is in units of gram (g) at most, suggesting that the column chromatography process is somewhat unsuitable for mass production. However, according to one embodiment of the present invention, it is possible to remove by-products easily through recrystallization, and to mass-produce 1-(2,4-dihydroxy-phenyl)-ethanone and the final product fisetin and fisetin derivatives.

According to one embodiment of the present invention, the recrystallization may be performed using an organic solvent selected from among hexane, pentane, ethyl ether and petroleum ether, and may preferably be performed using hexane.

According to one embodiment of the present invention, a first mixture containing 1-(2-hydroxy-4-methoxy-phenyl)-ethanone and 1-(2,4-dimethoxy-phenyl)-ethanone is produced by methylating the 1-(2,4-dihydroxy-phenyl)-ethanone. When the 1-(2,4-dihydroxy-phenyl)-ethanone is methylated, the hydroxyl group at the C-4 position of the phenyl ring is methylated, and the hydroxyl group at the C-2 position of the phenyl ring may be methylated (1-(2,4-dimethoxy-phenyl)-ethanone), or may not be methylated (1-(2-hydroxy-4-methoxy-phenyl)-ethanone).

When the hydroxyl group at the C-2 position of the phenyl ring is methylated (1-(2,4-dimethoxy-phenyl)-ethanone), cyclization with the hydroxyl group cannot occur in the process described below, and thus the 1-(2,4-dimethoxy-phenyl)-ethanone is a by-product. In a conventional art, this by-product is removed by purification, and then fisetin or fisetin derivatives is produced using only 1-(2-hydroxy-4-methoxy-phenyl)-ethanone, that is, paeonol.

However, according to one embodiment of the present invention, the 1-(2,4-dimethoxy-phenyl)-ethanone may be removed during post-treatment in a subsequent reaction, and thus fisetin or fisetin derivatives may be produced without a separate purification process.

According to one embodiment of the present invention, the methylation may be performed in a solution containing dimethyl sulfate, an inorganic base, and an organic solvent. The dimethyl sulfuric acid may be a source of a methyl group, and the inorganic base enables the compound to be weakly basic in nature while being ionized in the organic solvent. For example, potassium carbonate, sodium carbonate, cesium carbonate, or the like may be used as the inorganic base. The organic solvent is not particularly limited, and may be polar or non-polar. For example, acetone may be used as the organic solvent.

According to one embodiment of the present invention, the methylation may be performed at a temperature of 50 to 100° C. for 5 to 15 hours. When the methylation is performed under the temperature and time conditions within the above ranges, the methylation reaction may proceed smoothly.

The first mixture contains 1-(2-hydroxy-4-methoxy-phenyl)-ethanone and 1-(2,4-dimethoxy-phenyl)-ethanone, and 1-(2,4-dimethoxy-phenyl)-ethanone may be contained in the first mixture in an amount of 5 to 15 parts by weight based on 100 parts by weight of 1-(2-hydroxy-4-methoxy-phenyl)-ethanone. When 1-(2,4-dimethoxy-phenyl)-ethanone is contained in an amount within the above range, 1-(2,4-dimethoxy-phenyl)-ethanone may be removed during post-treatment in a subsequent reaction, and thus fisetin or fisetin derivatives may be produced without a separate purification process.

Next, the first mixture and a benzaldehyde compound represented by the following Formula 2 are added to and reacted with a basic solution, thus producing a second mixture containing a chalcone compound.

[Formula 2]

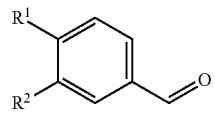

In Formula 2 above, $R^1$ and $R^2$ are each independently an alkoxy group containing a linear or branched alkyl group having 1 to 4 carbon atoms or a cyclic alkyl group having 3 to 6 carbon atoms; or a hydrogen atom. That is, the benzaldehyde compound may be benzaldehyde, dimethoxy benzaldehyde, methoxy benzaldehyde, diethoxy benzaldehyde, ethoxy benzaldehyde, dipropoxy benzaldehyde, propoxy benzaldehyde, isopropoxy benzaldehyde, dibutoxy benzaldehyde, butoxy benzaldehyde, cyclopropoxy benzaldehyde, dicyclobutoxy benzaldehyde, cyclopentoxy benzaldehyde, or cyclohexyloxy benzaldehyde. However, the benzaldehyde compound is not limited to the above-listed compound, and may preferably be dimethoxy benzaldehyde, methoxy benzaldehyde, or benzaldehyde.

According to one embodiment of the present invention, the chalcone compound may be produced by an aldol condensation reaction between 1-(2-hydroxy-4-methoxy-phenyl)-ethanone and the benzaldehyde compound. Specifically, the acyl group of 1-(2-hydroxy-4-methoxy-phenyl)-ethanone and the aldehyde group of the benzaldehyde compound may react with each other to produce a chalcone compound containing an α,β-unsaturated carbonyl group.

According to one embodiment of the present invention, the chalcone compound may be represented by the following Formula 5:

[Formula 5]

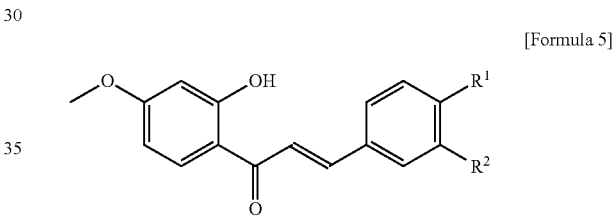

wherein $R^1$ and $R^2$ are each independently an alkoxy group containing a linear or branched alkyl group having 1 to 4 carbon atoms or a cyclic alkyl group having 3 to 6 carbon atoms; or a hydrogen atom.

According to one embodiment of the present invention, the basic solution may contain an organic solvent and a basic compound. As the organic solvent, a polar organic solvent such as methanol or ethanol may be used, and as the basic compound, sodium hydroxide, potassium hydroxide or the like may be used, but the present invention is not limited thereto.

According to one embodiment of the present invention, the basic solution may contain a basic compound at a concentration of 0.1 N to 1.0 N. When the basic compound is contained at a concentration within the above range, it is possible to obtain the product in high yield.

According to one embodiment of the present invention, the aldol condensation reaction may be performed at a temperature of 80° C. to 120° C. for 40 hours to 55 hours. When the reaction is performed under temperature and time conditions within the above ranges, the chalcone compound may be successfully formed.

After completion of the aldol condensation reaction, the resulting product may be cooled to room temperature.

After completion of the reaction, the second mixture containing the chalcone compound may be used directly without a separate purification process. In a conventional art, column chromatography is used to remove by-products. However, according to one embodiment of the present invention, even if by-products are present, they have no significant effect on the yield, and fisetin or fisetin derivatives may be produced in high yield.

Next, hydrogen peroxide is added to the second mixture containing the chalcone compound, thus producing fisetin derivatives represented by the following Formula 3:

[Formula 3]

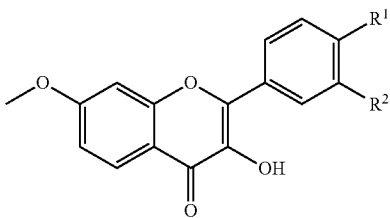

In Formula 3 above, $R^1$ and $R^2$ are each independently an alkoxy group containing a linear or branched alkyl group having 1 to 4 carbon atoms or a cyclic alkyl group having 3 to 6 carbon atoms; or a hydrogen atom.

When the hydrogen peroxide is added, a hydroxyl group may be introduced at the C-3 position by the Algar-Flynn-Oyamada reaction of the chalcone compound with hydrogen peroxide, and the fisetin derivative represented by Formula 3 may be produced through cyclization. Specifically, the carbon at the C-4 position may form a ring by bonding to the hydroxyl group contained in the chalcone compound, and a hydroxyl group may be introduced at the C-3 position, thereby producing the fisetin derivative represented by Formula 3.

According to one embodiment of the present invention, the hydrogen peroxide may be added in the form of an aqueous solution, or the basic aqueous solution may be added prior to addition of the hydrogen peroxide. Since the Algar-Flynn-Oyamada reaction may be performed more smoothly in a basic atmosphere, the hydrogen peroxide may be added after the basic atmosphere is created as described above.

The Algar-Flynn-Oyamada reaction may be performed at room temperature for 20 to 30 hours. The reaction may be performed with stirring, and when the reaction is performed for a time within the above range, the fisetin derivative may be successfully produced.

After the fisetin derivative represented by Formula 3 is produced, the fisetin derivative represented by Formula 3 may be obtained through steps of: neutralizing by addition of a strongly acidic compound; and filtering.

According to one embodiment of the present invention, the strongly acidic compound may be added in the form of a solution, and the type thereof is not particularly limited. For example, hydrochloric acid may be used. The strongly acidic compound may be added for neutralization until pH 7 is reached.

According to one embodiment of the present invention, the fisetin derivative represented by Formula 3 may be obtained as a solid content through filtration, and the filtration may be performed by a method used in the art.

According to one embodiment of the present invention, the method may further include a step of producing a fisetin or fisetin derivative represented by the following Formula 4 by dealkylating the fisetin derivative represented by Formula 3:

[Formula 4]

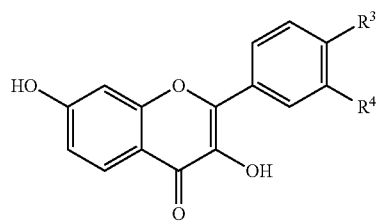

In Formula 4 above, $R^3$ and $R^4$ are each independently a hydroxyl group or a hydrogen atom.

When $R^3$ and $R^4$ in Formula 4 above are each independently a hydroxyl group, the compound represented by Formula 4 may be fisetin.

According to one embodiment of the present invention, the dealkylation may be performed by allowing pyridine hydrochloride to react with the fisetin derivative represented by Formula 3 above. Specifically, the dealkylation reaction may be performed on a solid mixture obtained by mixing the fisetin derivative represented by Formula 3 with the pyridine hydrochloride solid.

According to one embodiment of the present invention, the methyl group of a methoxy group derived from 1-(2,4-dihydroxy-phenyl)-ethanone may be removed through demethylation and converted into a hydroxyl group, and the alkyl group of an alkoxy group ($R^1$ and/or $R^2$) derived from the benzaldehyde compound may be removed and converted into a hydroxyl group.

According to one embodiment of the present invention, the demethylation may be performed at a temperature of 130° C. to 180° C. for 10 hours to 15 hours. When the demethylation reaction is performed at a temperature within the above range, fisetin or fisetin derivatives may be obtained in high yield.

According to the method for producing fisetin or fisetin derivatives according to one embodiment of the present invention, fisetin or fisetin derivatives may be produced in a high yield of 80% to 99%, 90% to 99%, or 97% to 99%.

Hereinafter, the present invention will be described in detail with reference to examples. However, the examples according to the present invention may be modified into various different forms, and the scope of the present invention is not interpreted as being limited to the examples described below. The examples of the present specification are provided to more completely explain the present invention to those skilled in the art.

Materials Used and Common Reaction Conditions

Reactants and solvents were purchased from Sigma-Aldrich, TCI, Samcheon Chemical, and Alfa Aesar, and used without further purification. Reactions were monitored by thin layer chromatography on 0.5 mm Merck silica gel plates (60F25) using UV light at 254 nm. $^1$H NMR spectra were recorded using a JEOL superconducting magnet JMTC-400/54/JJ/YH (400 MHz). Chemical shifts were reported in ppm downfield from tetramethylsilane (TMS), and coupling constant (J) was recorded in Hertz.

Production of 1-(2,4-dihydroxy-phenyl)-ethanone 1,3-dihydroxy benzene (20.0 g, 181.7 mmol) and acetic anhydride (18.55 g, 181.7 mmol) were dissolved in 80 mL of ethyl acetate. $BF_3$-$Et_2O$ (51.6 g, 363.4 mmol) in ethyl acetate (20 mL) was added dropwise thereto at room temperature, and the reaction mixture was stirred at 60° C. for 12 hours. The resulting product was diluted with water (100 mL) and extracted twice with ethyl acetate (200 mL). The organic layer was washed twice with 200 mL of a saturated aqueous solution of $NaHCO_3$. Water was removed from the organic layer using $MgSO_4$ and the residue was filtered. The filtrate was concentrated under reduced pressure to obtain an oily residue which was then recrystallized from hexane to obtain 1-(2,4-dihydroxy-phenyl)-ethanone (26.3 g, 95% yield). $^1$H-NMR (400 MHz, DMSO) δ: 2.47 (3H, m), 6.20 (1H, d, J=2.32 Hz), 6.35 (1H, dd, J=8.8, 2.32 Hz), 7.73 (1H, d, J=8.8 Hz), 10.60 (1H, s), 12.57 (1H, s).

Production of a mixture of 1-(2-hydroxy-4-methoxy-phenyl)-ethanone and 1-(2,4-dimethoxy-phenyl)-ethanone Potassium carbonate (17.0 g, 122.9 mmol) was added to a solution of 1-(2,4-dihydroxy-phenyl)-ethanone (18.7 g, 122.9 mmol) in acetone (100 mL). Dimethyl sulfuric acid (17.1 g, 135.2 mmol) was added to the reaction vessel in 3 portions over 1 hour, and the mixture was stirred at 60° C. for 12 hours. Acetone was removed from the resulting mixture in vacuo. Then, the residue was diluted with water (200 mL) and extracted twice with ethyl acetate (200 mL). The organic layer was washed with brine (30 mL). Water was removed from the organic layer using $MgSO_4$ and the residue was filtered. The filtrate was concentrated under reduced pressure to obtain a mixture (22.3 g) of 1-(2-hydroxy-4-methoxy-phenyl)-ethanone and 1-(2,4-dimethoxy-phenyl)-ethanone. $^1$H-NMR (400 MHz, CDCl3) δ: 2.54 (3H, s), 3.82 (3H, s), 6.44 (2H, dd, J=2.16, 1.86 Hz), 7.63 (1H, d, J=8.68 Hz), 12.74 (1H, s).

Example 1

Production of 2-(3,4-dimethoxy-phenyl)-3-hydroxy-7-methoxy-chromen-4-one (Formula 3-1)

[Formula 3-1]

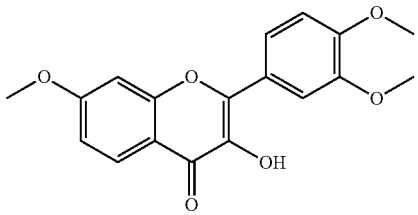

An oil mixture (22.3 g, 134.2 mmol) of 1-(2-hydroxy-4-methoxy-phenyl)-ethanone and 1-(2,4-dimethoxy-phenyl)-ethanone (22.3 g, 134.2 mmol), and 3,4-dimethoxybenzaldehyde (29.0 g, 174.4 mmol) were added to a solution of potassium hydroxide (113.0 g, 2,013 mmol) in methanol (350 mL) and stirred at 90° C. for 48 hours. The reaction mixture was cooled to room temperature, and then sodium hydroxide (0.5 N, 580 mL) and hydrogen peroxide (35%, 43 mL) were sequentially added thereto. The mixture was stirred at room temperature for 24 hours and neutralized by adding concentrated HCl until pH 7 was reached. The resulting product was filtered and 2-(3,4-dimethoxy-phenyl)-3-hydroxy-7-methoxy-chromen-4-one (17.0 g, 42% yield relative to 1-(2,4-dihydroxy-phenyl)-ethanone) was obtained as a solid. $^1$H-NMR (400 MHz, DMSO) δ: 3.82 (6H, d, J=2.12 Hz), 3.89 (3H, s), 7.02 (1H, dd, J=2.08, 2.04 Hz), 7.12 (1H, d, J=8.68 Hz), 7.27 (1H, d, J=1.88 Hz), 7.77 (1H, d, J=1.36 Hz), 7.84 (1H, dd, J=1.56, 1.56 Hz), 7.96 (1H, d, J=8.92 Hz), 9.28 (1H, s).

Production of 2-(3,4-dihydroxy-phenyl)-3,7-dihydroxy-chromen-4-one (fisetin, Formula 1)

[Formula 1]

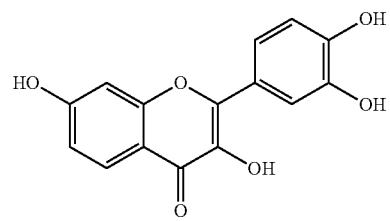

2-(3,4-dimethoxy-phenyl)-3-hydroxy-7-methoxy-chromen-4-one (17.0 g, 51.78 mmol) and pyridine hydrochloride (35.0 g) were added and stirred at 160° C. for 12 hours. Water (600 mL) was added to the obtained solid mixture, followed by stirring at room temperature for 2 hours. The resulting mixture was filtered to obtain fisetin (14.4 g, 97%) as a solid. $^1$H-NMR (400 MHz, DMSO) δ: 6.87 (3H, t, J=7.12 Hz), 7.51 (1H, dd, J=1.72, 1.68 Hz), 7.64 (1H, s), 7.89 (1H, d, J=9.32 Hz), 8.98 (1H, s), 9.21 (1H, s), 9.44 (1H, s), 10.68 (1H, s); HRMS (ES+) calculated for $C_{15}H_{10}O_6$: 286.0477, found: 287.0544.

Example 2

Production of 3-hydroxy-7-methoxy-2-(4-methoxy-phenyl)-chromen-4-one (Formula 3-2)

[Formula 3-2]

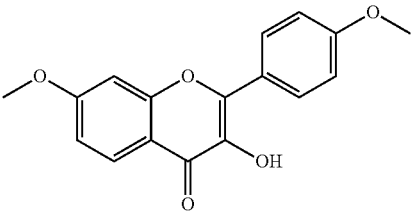

An oil mixture (3.0 g, 18.05 mmol) of 1-(2-hydroxy-4-methoxy-phenyl)-ethanone and 1-(2,4-dimethoxy-phenyl)-ethanone, and 4-methoxybenzaldehyde (3.2 g, 23.47 mmol) were added to a solution of potassium hydroxide (15.2 g, 270.1 mmol) in methanol (70 mL) and stirred at 90° C. for 48 hours. The reaction mixture was cooled to room temperature, and sodium hydroxide (0.5 N, 80 mL) and hydrogen peroxide (35%, 6 mL) were sequentially added thereto. The mixture was stirred at room temperature for 24 hours and neutralized by adding concentrated HCl until pH 7 was reached. The resulting mixture was filtered to obtain 3-hydroxy-7-methoxy-2-(4-methoxy-phenyl)-chromen-4-one (2.0 g, 40.4% yield) as a solid. $^1$H-NMR (400 MHz, DMSO) δ: 3.81 (3H, s), 3.88 (3H, s), 7.02 (1H, dd, J=2.24, 2.2 Hz), 7.10 (2H, d, J=8.96 Hz), 7.25 (1H, d, J=2.16 Hz), 7.96 (1H, d, J=8.92 Hz), 8.17 (2H, d, J=8.96 Hz), 9.30 (1H, s).

Production of 3,7-dihydroxy-2-(4-hydroxy-phenyl)-chromen-4-one (Formula 4-1)

[Formula 4-1]

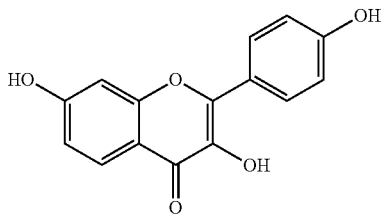

3-hydroxy-7-methoxy-2-(4-methoxy-phenyl)-chromen-4-one (1.0 g, 3.39 mmol) and pyridine hydrochloride (6.0 g) were added and stirred at 160° C. for 12 hours. Water (50 mL) was added to the obtained solid mixture, followed by stirring at room temperature for 2 hours. The resulting mixture was filtered to obtain 3,7-dihydroxy-2-(4-hydroxy-phenyl)-chromen-4-one (889 mg, 97%) as a solid. $^1$H-NMR (400 MHz, DMSO) δ: 6.85 (1H, d, J=2.0 Hz), 6.87 (1H, s), 6.90 (2H, t, J=2.16 Hz), 7.89 (1H, d, J=8.64 Hz), 8.02 (2H, d, J=8.8 Hz), 9.04 (1H, s), 9.99 (1H, s), 10.71 (1H, s).

Example 3

Production of 3-hydroxy-7-methoxy-2-phenyl-chromen-4-one (Formula 3-3)

[Formula 3-3]

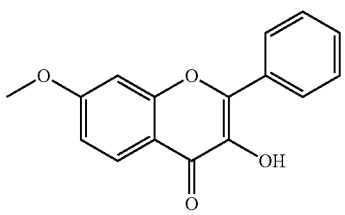

An oil mixture (3.0 g, 18.05 mmol) of 1-(2-hydroxy-4-methoxy-phenyl)-ethanone and 1-(2,4-dimethoxy-phenyl)-ethanone, and benzaldehyde (3.8 g, 36.10 mmol) were added to a solution of potassium hydroxide (15.2 g, 270.1 mmol) in methanol (70 mL) and stirred at 90° C. for 48 hours. The reaction mixture was cooled to room temperature, and sodium hydroxide (0.5 N, 80 mL) and hydrogen peroxide (35%, 6 mL) were sequentially added thereto. The mixture was stirred at room temperature for 24 hours and neutralized by adding concentrated HCl until pH 7 was reached. The resulting mixture was filtered to obtain 3-hydroxy-7-methoxy-2-phenyl-chromen-4-one (1.85 g, 41.6% yield) as a solid. $^1$H-NMR (400 MHz, DMSO) δ: 3.88 (3H, s), 7.03 (1H, dd, J=2.24, 2.24 Hz), 7.26 (1H, d, J=2.16 Hz), 7.47 (1H, t, J=7.24 Hz), 7.55 (2H, t, J=7.28 Hz), 7.98 (1H, d, J=8.92 Hz), 8.19 (2H, d, J=7.6 Hz), 9.48 (1H, s).

Production of 3,7-dihydroxy-2-phenyl-chromen-4-one (Formula 4-2)

[Formula 4-2]

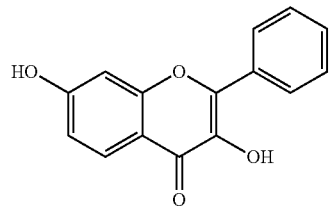

3-hydroxy-7-methoxy-2-phenyl-chromen-4-one (1.0 g, 3.39 mmol) and pyridine hydrochloride (6.0 g) were added and stirred at 160° C. for 12 hours. Water (50 mL) was added to the obtained solid mixture, followed by stirring at room temperature for 2 hours. The resulting mixture was filtered to obtain 3,7-dihydroxy-2-phenyl-chromen-4-one (836 mg, 97% yield) as a solid. $^1$H-NMR (400 MHz, DMSO) δ: 6.90 (1H, dd, J=2.24, 2.24 Hz), 6.92 (1H, d, J=2.04 Hz), 7.46 (1H, m), 7.54 (2H, m), 7.93 (1H, d, J=8.72 Hz), 8.13 (1H, t, J=1.36 Hz), 8.15 (1H, t, J=1.44 Hz), 9.33 (1H, s), 10.78 (1H, s).

Although the present disclosure has been described above by way of limited embodiments, the present disclosure is not limited thereto. It should be understood that the present disclosure can be variously changed and modified by those skilled in the art without departing from the technical sprit of the present disclosure and the range of equivalents to the appended claims.

What is claimed is:

1. A method for producing fisetin or fisetin derivatives, the method comprising steps of:
    producing a first mixture containing 1-(2-hydroxy-4-methoxy-phenyl)-ethanone and 1-(2,4-dimethoxy-phenyl)-ethanone by methylating 1-(2,4-dihydroxy-phenyl)-ethanone;
    producing a second mixture containing a chalcone compound by adding the first mixture and a benzaldehyde compound represented by the following Formula 2 to a basic solution and allowing them to react; and
    producing fisetin derivatives represented by the following Formula 3 by adding hydrogen peroxide to the second mixture:

[Formula 2]

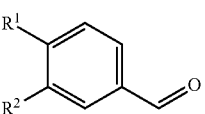

[Formula 3]

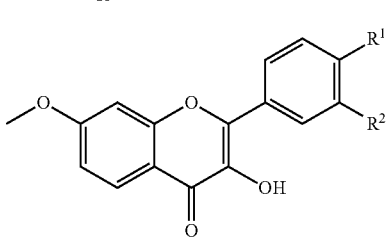

wherein R¹ and R² are each independently an alkoxy group containing a linear or branched alkyl group having 1 to 4 carbon atoms or a cyclic alkyl group having 3 to 6 carbon atoms; or a hydrogen atom.

2. The method of claim 1, wherein the 1-(2,4-dihydroxy-phenyl)-ethanone is produced by Friedel-Crafts acylation of resorcinol and recrystallization.

3. The method of claim 2, wherein the recrystallization is performed using an organic solvent selected from among hexane, pentane, ethyl ether and petroleum ether.

4. The method of claim 1, wherein the methylation is performed in a solution containing dimethyl sulfate, an inorganic base and an organic solvent.

5. The method of claim 1, wherein the methylation is performed at a temperature of 50 to 100° C. for 5 to 15 hours.

6. The method of claim 1, wherein the chalcone compound is produced by an aldol condensation reaction between the 1-(2-hydroxy-4-methoxy-phenyl)-ethanone and the benzaldehyde compound.

7. The method of claim 1, wherein the basic solution contains a basic compound at a concentration of 0.1 N to 1.0 N.

8. The method of claim 1, further comprising a step of producing fisetin or fisetin derivatives represented by the following Formula 4 by dealkylating the fisetin derivative represented by Formula 3:

[Formula 4]

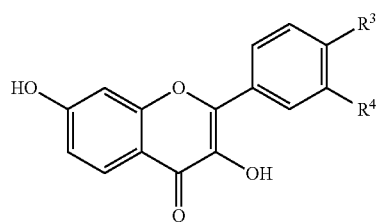

wherein R³ and R⁴ are each independently a hydroxyl group or a hydrogen atom.

9. The method of claim 8, wherein the dealkylation is performed by allowing pyridine hydrochloride to react with the fisetin derivative represented by Formula 3.

* * * * *